United States Patent [19]

Chomczynski

[11] Patent Number: 5,945,515

[45] Date of Patent: Aug. 31, 1999

[54] PRODUCT AND PROCESS FOR ISOLATING DNA, RNA AND PROTEINS

[76] Inventor: Piotr Chomczynski, 778 Avon Fields Ln., Cincinnati, Ohio 45229

[21] Appl. No.: 08/509,164

[22] Filed: Jul. 31, 1995

[51] Int. Cl.$^6$ .............................. C12P 19/34; C12N 15/10
[52] U.S. Cl. .......................... 530/412; 530/413; 530/419; 530/421; 435/270; 536/25; 536/41; 935/19; 935/20
[58] Field of Search ........................ 935/19, 20; 530/413, 530/412, 419, 421; 435/270; 536/25, 41

[56] References Cited

U.S. PATENT DOCUMENTS

| | | | |
|---|---|---|---|
| 3,147,185 | 9/1964 | Charney | 536/24 |
| 3,389,133 | 6/1968 | Gutcho | 536/24 |
| 4,843,155 | 6/1989 | Chomczynski | 536/27 |
| 5,010,183 | 4/1991 | Macfarlane | 536/27 |
| 5,128,247 | 7/1992 | Koller | 435/91 |
| 5,130,423 | 7/1992 | Van Ness et al. | 536/27 |
| 5,162,507 | 11/1992 | Wolfe et al. | 530/412 |
| 5,234,809 | 8/1993 | Boom et al. | 435/91 |
| 5,346,994 | 9/1994 | Chomczynski | 530/419 |
| 5,407,810 | 4/1995 | Builder et al. | 435/69.1 |

FOREIGN PATENT DOCUMENTS

| | | |
|---|---|---|
| 0554034 | 1/1993 | European Pat. Off. . |
| 9200983 | 1/1992 | WIPO . |

OTHER PUBLICATIONS

James E. Nelson et al., "Purification of Cloned and Genomic DNA by Guanidine Thiocyanate/Isobutyl Alcohol Fractionation," 1992, Analytical Biochemistry, pp. 197–201.

Michael W. Lema et al., "A general method for the extraction of DNA from bacteria," 1994, Journal of Microbiological Methods, pp. 167–172.

Coombs, L.M. et al., "Simultaneous Isolation of DNA, RNA, And Antigenic Protein Exhibiting Kinase Activity From Small Tumor Samples Using Guanidine Isothiocyanate", Anal. Biochem 188, pp. 338–343 (1990).

J. Sambrook et al., "Molecular Cloning", Cold Spring Harbor Press, 2nd Ed., pp. 9.14–9.23 (1989).

F. M. Ausubel et al., "Current Protocols In Molecular Biology", John Wiley & Sons, Inc., vol. 1, pp. 2.2.1–2.4.5 (1994).

Analects vol. 22 No. 4, Pharmacia Biotech (1994).

D.D.L. Bowtell, "Rapid Isolation of Eukaryotic DNA", Anal. Biochem. 162, pp. 463–465 (1987).

J. M. Chirgwin et al., "Isolation of Biologically Active Ribonucleic Acid from Sources Enriched in Ribonuclease", Biochemistry 18, pp. 5294–5299 (1979).

T. A. Ciulla et al., "A Simple Method for DNA Purification from Peripheral Blood", Anal. Biochem. 174, pp. 485–488 (1988).

J. Sambrook et al., "Molecular Cloning" 2nd Ed., Cold Spring Harbor Press, pp. 7.2–7.25 (1989).

F. M. Ausubel et al., "Current Protocols In Molecular Biology", vol. 1, John Wiley & Son, Inc., pp. 4.0.3–4.4.7 (1994).

P. Chomczynski, "Solubilization in formamide protects RNA from degradation", Nucleic Acids Research, vol. 20, No. 14, pp. 3791–3792 (1992).

M. Sela et al., "The Correlation of Ribonuclease Activity With Specific Aspects of Tertiary Structure," Biochem. Biophys. Acta 26, pp. 506–511 (1957).

R. A. Cox, "The Use of Guanidinium Chloride in the Isolation of Nucleic Acids," Methods of Enzymology 12(B):120–129 (1968).

N.C. Nicolaides et al., "A Simple, Efficient Method for the Separate Isolation of RNA and DNA from the Same Cells," Biotechniques 8, pp. 154–156 (1990).

S. Raha et al., "Simultaneous Isolation of Total Cellular RNA and DNA from Tissue Culture Cells Using Phenol and Lithium Chloride," Gene Anal. Techn. 7, pp. 173–177 (1990).

V. T.W. Chan et al., "Simultaneous Extraction from Clinical Biopsies of High–Molecular–Weught DNA and RNA: Comparative Characterization by Biotinylated and $^{32}$P–Labeled Probes on Southern and Northern Blots," Anal. Biochem. 168, pp. 16–24 (1988).

B. Attardi et al., "Rapid Stimulatory Effect of Activin–A on Messenger RNA Encoding the Follicle–Stimulating Hormone β–Subunit in Rat Pituitary Cell Cultures," Molec. Endocrin. 4, pp. 721–726 (1990).

B. Attardi et al., "Effects of Progesterone on the Estradiol–Induced Follicle–Stimulating Hormone (FSH) Surge and FSHβ Messenger Ribonucleic Acid in the Rat," Endocrinology 126, pp. 2281–2287 (1990).

J.R. Feramisco et al., "Extraction, Purification, And Analysis of mRNA From Eukaryotic Cells", pp. 194–195.

N.K. Kochetkov et al., "Organic Chemistry of Nucleic Acids", Part A, Plenum Press, 1971, pp. 23–28.

Cole, K. D. Purification of plasmid and high molecular mass DNA using PEG–salt two–pahse extraction. BioTechniques, 11:18–24 (1991).

Pepinsky, R. B. Selective precipitation of proteins from guanidine hydrochloride solutions with ethanol. Anal. Biochem., 195:177–181 (1991).

Chomczynski et al. (1987), Anal. Biochem. 162, 156.

*Primary Examiner*—Elizabeth Kemmerer
*Assistant Examiner*—David S. Romeo
*Attorney, Agent, or Firm*—Wood, Herron & Evans, L.L.P.

[57] ABSTRACT

Solutions and methods are disclosed for the effective, simple isolation/extraction of DNA, RNA and proteins from a single biological material sample, such as cells, tissues and biological fluids. The preferred solutions include effective amounts of a chaotropic agent(s), buffer, reducing agent, and may or may not include an organic solvent. Genomic DNA and total RNA can be isolated utilizing the solutions and methods of the invention in as little as 20 minutes, and proteins in as little as 30 minutes.

22 Claims, 1 Drawing Sheet

FIG.1B RT-PCR GAPDH

FIG.1C PCR GH

FIG.1D Western prolactin

FIG.2B Northern GH mRNA

FIG.2C Southern GH DNA fragment

FIG.2D Western GH

PRODUCT AND PROCESS FOR ISOLATING DNA, RNA AND PROTEINS

FIELD OF THE INVENTION

The invention relates to compositions and methods for isolating nucleic acids (both RNA and DNA) and proteins from biological materials. And more particularly, the invention relates to nucleic acid and protein isolation methods employing non-toxic chaotropic agents.

BACKGROUND OF THE INVENTION

The continuous advances in molecular biology, biotechnology and clinical research have resulted in an ever increasing number of uses for DNA, RNA and proteins. For example, polymerase chain reaction (PCR) technology has dramatically expanded the use of DNA and RNA in basic research, in clinical diagnostics such as detection of messenger RNA (mRNA) by reverse transcription PCR (RT-PCR), and the use of PCR in detection of genetic defects. In the protein field, identification of proteins by Western blotting has become an important tool in studying gene expression in basic research and identification of specific proteins for diagnostic purposes, as exemplified by viral protein detection.

The increased use of RNA, DNA and proteins has created a need for fast, simple and reliable methods and reagents for isolating DNA, RNA and proteins. In many applications, collecting the biological material sample and subsequent analysis thereof would be substantially simplified if the three cellular components (RNA, DNA and proteins) could be simultaneously isolated from a single sample. The simultaneous isolation is especially important when the sample size is so small, such as in biopsy, that it precludes its separation into smaller samples to perform separate isolation protocols for DNA, RNA and proteins.

There are known methods for isolating DNA, RNA and proteins from a single biological material sample. One such method is described in Coombs, L. M., et al.: "Simultaneous Isolation of DNA, RNA and Antigenic Protein Exhibiting Kinase Activity from Small Tumor Samples Using Guanidine Isothiocyanate", *Anal. Biochem.*, 188, 338–343 (1990). The Coombs et al. method is based on ultracentrifugation of the sample homogenate in a guanidine-cesium chloride solution. The sample is homogenized in 4M guanidine thiocyanate and then overlayered on a cesium chloride (CsCl) solution and centrifuged at>100,000 g for about 18 hours. Following centrifugation, DNA, RNA and proteins are separated and purified over the next 12–24 hours. This method has several limitations or drawbacks, including the prolonged time required for isolation and the limited number and size of samples which can be processed with an ultracentrifuge. Also, the high cost of an ultracentrifuge may be prohibitive in certain circumstances.

Another method for the simultaneous isolation of DNA, RNA and proteins from a single biological material sample is the subject of my earlier U.S. Pat. No. 5,346,994 (the '994 patent). That method is based on liquid-phase separation using phenol and guanidine thiocyanate. A biological sample is homogenized in the aqueous solution of phenol and guanidine thiocyanate and the homogenate thereafter is mixed with chloroform. Following centrifugation, the homogenate separates into an organic phase, an interphase and an aqueous phase. Proteins are sequestrated into the organic phase, DNA into the interphase and RNA into the aqueous phase. Next, each component is precipitated from the corresponding phase using ethanol and is then washed. The whole procedure can be completed in about 2–3 hours, and is especially useful for the isolation of high quality RNA from a variety of sources. One drawback to this method is the use of highly toxic phenol.

There are many known methods for the separate isolation of DNA, RNA and proteins from biological material; i.e., protocols for isolating a single one of these components from a sample. In typical DNA isolation methods, a biological sample is lysed in a lysing solution and then the DNA is isolated from the lysate according to any one of a variety of multi-step protocols, which may take from one hour to several days to complete. Frequently recommended DNA isolation methods involve the use of toxic phenol. See, Sambrook, J. et al., "Molecular Cloning", Vol. 2, pp. 9.14–9.23, Cold Spring Harbor Laboratory Press (1989) and Ausubel, Frederick M. et al., "Current Protocols in Molecular Biology", Vol. 1, pp. 2.2.1–2.4.5, John Wiley & Sons, Inc. (1994). Typically, a biological sample is lysed in a detergent solution and the protein component of the lysate is digested with proteinase for 12–18 hours. Next, the lysate is extracted with phenol to remove most of the cellular components, and the remaining aqueous phase is processed further to isolate DNA. In another method, described in Van Ness et al. U.S. Pat. No. 5,130,423, non-corrosive phenol derivatives are used for the isolation of nucleic acids. The resulting preparation is a mix of RNA and DNA.

DNA isolation methods utilizing non-corrosive chaotropic agents have also been developed. These methods, which are based on the use of guanidine salts, urea and sodium iodide, involve lysis of a biological sample in a chaotropic aqueous solution and subsequent precipitation of the crude DNA fraction with a lower alcohol. The final purification of the precipitated, crude DNA fraction can be achieved by any one of several methods, including column chromatography as described in "RapidPrep™ Genomic DNA Isolation Kits For Cells and Tissue: Versatility at Your Fingertips!", *Analects*, Vol 22, No. 4, Pharmacia Biotech, 1994, or exposure of the crude DNA to a polyanion-containing protein as described in Koller U.S. Pat. NO. 5,128,247.

Yet another method of DNA isolation, which is described in Botwell, D. D. L., "Rapid Isolation of Eukaryotic DNA", *Anal. Biochem.* 162, 463–465 (1987) involves lysing cells in 6M guanidine hydrochloride, precipitating DNA from the lysate at acid pH by adding 2.5 volumes of ethanol, and washing the DNA with ethanol. It is believed that the resulting DNA may be contaminated, however, with a low molecular weight material such as RNA and pigments. This conclusion is in agreement with the well known report showing that under similar conditions RNA can be precipitated from cell or tissue lysate. See Chirgwin, J. M. et al., "Isolation of Biologically Active Ribonucleic Acid from Sources Enriched in Ribonuclease", Dept. of Biochemistry and Biophysics, Univ. of California, Vol. 18, No. 24, pp. 5294–5299 (1979).

Sodium iodide, another chaotropic agent, has been used in DNA isolation, but its use requires an additional purification step consisting of adsorption of the isolated DNA on glass beads. Although this method is relatively simple, it results in a low yield of isolated DNA.

In still another approach, the bulk of cytoplasmic proteins and RNA are removed by lysing cell samples in a detergent solution. The lysate is then fractionated into the nuclear and cytoplasmic fractions. And thereafter, the DNA is purified by dissolving the nuclear fraction in a chaotropic solution, precipitating and washing with ethanol. This method, described in Ciulla, T. A. et al., "A Simple Method for DNA Purification from Peripheral Blood", *Anal. Biochem.* 174, 485–488 (1988), can be completed in about 2 hours and is useful for isolating DNA from whole blood.

Known techniques for isolating RNA typically utilize either guanidine salts or phenol extraction, as described for example in Sambrook, J. et al., "Molecular Cloning", Vol. 1, pp. 7.3–7.24, Cold Spring Harbor Laboratory Press (1989) and Ausubel, F. M. et al., "Current Protocols in Molecular Biology", Vol. 1, pp. 4.0.3–4.4.7, John Wiley & Sons, Inc. (1994). Phenol-based techniques are multi-step procedures requiring several hours or days to complete. Similarly, the guanidine-based RNA isolation methods require at least several hours and take many steps to complete. In my earlier U.S. Pat. No. 4,843,155, phenol and guanidine procedures were uniquely combined, resulting in a simple method of total RNA isolation which can be completed in 3 hours. The method of the '155 patent was further improved upon in my '994 patent, which allows for completion of the RNA isolation in about 1 hour.

There are also known techniques for the simultaneous isolation of DNA and RNA, as referenced in my earlier '994 patent, the disclosures of which are incorporated herein by reference. All of these techniques utilize phenol extraction as a necessary step for isolating RNA and DNA free of protein contamination.

Heretofore, it has been the commonly accepted view that precipitation of nucleic acids from chaotropic solvents does not result in pure nucleic acid preparations. Contrary to this view, however, the present inventor has found that under certain conditions, as described in full detail herein, the use of chaotropic agents alone will result in isolation of assay ready, high quality DNA and RNA. This unexpected finding led to the development of a very simple, effective method and product for the simultaneous isolation of DNA, RNA and proteins from a single sample for subsequent use in molecular biology, biotechnology, clinical research and other applications.

SUMMARY OF THE INVENTION

The products and methods of the present invention provide a highly effective, simple means of extracting DNA, RNA and proteins from a single biological material sample, such as cells, tissues and biological fluids. Advantageously, these results can be achieved without the use of toxic or corrosive reagents and without the use of expensive ultracentrifugation equipment. Genomic DNA and total RNA can be isolated utilizing the products and methods of the invention in as little as 20 minutes, and proteins in as little as 30 minutes. These results are substantially faster than existing methods for the simultaneous isolation of DNA, RNA and proteins. The invention is also applicable to the separate isolation of RNA only, DNA only, proteins only or any combination of two of these cellular components. The resulting genomic DNA and total RNA isolated utilizing the methods and products of the invention are of high quality suitable for use in research, biotechnology, etc. The invention is in part based on the unexpected finding that utilizing the products of the invention, RNA is precipitated prior to DNA, which is contrary to prior art methodologies. In particular, the finding that the solvent solution of the present invention precipitates RNA prior to DNA is in striking contrast to the described prior art such as Koller U.S. Pat. No. 5,128,247, wherein it describes that DNA exhibits a lower solubility than RNA and apparently can be precipitated more easily than RNA. Furthermore, substantially lower amounts of organic solvents are required to effect the precipitation of the cellular components.

In its broadest aspects, the invention encompasses solutions for isolating substantially pure and undegraded RNA, DNA and protein from biological materials, including tissue, cells and fluids. The solution preferably includes effective amounts of a chaotropic agent(s), buffer, reducing agent, and water (with or without organic solvent(s)). The chaotropic agent(s) act to dissociate proteins from nucleic acids (RNA and DNA) and inhibit the activity of nucleic acid degradation enzymes. The actions of the chaotropes are potentiated by the reducing agent present in the solvent solution. When the solution includes an organic solvent, its presence prevents solubilization of RNA, thereby making it possible to remove RNA from the homogenate formed when the tissue sample is homogenized in the solvent solution by a brief centrifugation step. When the solution does not include an organic solvent, the RNA is precipitated from the homogenate subsequent to homogenization by the addition of an organic solvent.

Preferred chaotropic agents for the solution include guanidine thiocyanate, guanidine hydrochloride, and mixtures thereof. These components may be supplemented with other chaotropes, such as urea or sodium iodide. The preferred concentration of chaotropes in the solution is in the range of about 2M–7M. Preferably, the reducing agent is non-toxic, such as 2-aminoethanethiol. If required, this can be substituted with 2-mercaptoethanol; however, this is a toxic composition. The reducing agent facilitates denaturization of RNase by the chaotropes and aids in the isolation of undegraded RNA.

The solution of the present invention preferably contains a sufficient amount of buffer to maintain the pH of the solution above about 6. For the simultaneous isolation of RNA, DNA and proteins, the pH should be maintained in the range of about 6–7.5. For the isolation of DNA alone, the effective pH range may be about 6–12. The preferred buffers for use in the solutions of the invention include tris-hydrochloric acid, sodium phosphate, sodium acetate, sodium tetraborate-boric acid and glycine-sodium hydroxide.

As stated, the solution may contain an organic solvent. The preferred solvents are lower alcohols such as methanol, ethanol and isopropanol. However, other water miscible solvents can be used which will achieve the desired effect, such as acetone, polyethylene glycol and dimethylsulfoxide, or mixtures of any of the foregoing. The effective concentration of organic solvents in the product of the invention is in the range of about 15–30% by volume.

The solution of the invention may contain additional components, including organic and inorganic salts such as sodium chloride, potassium chloride, ammonium chloride, sodium phosphate, sodium acetate, sodium nitrite, lithium chloride, and sodium bromide. Furthermore, compatible detergents such as sarcosines and polyoxyethylenesorbitan, and chelating agents such as ethylenediamine tetraacetic acid and citric acid can be utilized to promote tissue solubilization and precipitation of nucleic acids.

In another aspect, the invention encompasses methods of isolating substantially pure RNA, DNA and proteins from biological material samples. Utilizing the solutions of the present invention, and particularly those wherein the solution includes an organic solvent, the method includes an initial step of homogenizing a biological material sample in the solution to form an homogenate. The presence of the organic solvent prevents solubilization of RNA, thereby making it possible to remove RNA from the homogenate by brief centrifugation (sedimentation). Thereafter, DNA is precipitated from the remaining homogenate by adding an effective amount of an organic solvent and recovering the precipitated DNA by brief centrifugation (sedimentation). Finally, adding an effective amount of an organic solvent to the remaining homogenate precipitates proteins therefrom. The successive addition of organic solvents to precipitate genomic DNA and proteins from the post-RNA homogenate require a limited amount of the organic solvent. Following a wash with ethanol, the three cellular components are each separately and fully ready for use in molecular biology, biotechnology and clinical research applications. Preferably, the organic solvent utilized to precipitate DNA is added in a ratio of about 0.15–0.3 volumes of solvent per one volume of initial homogenate. The organic solvent added to precipitate proteins is preferably added in the ratio of about 3–4 volumes of solvent per one volume of initial homogenate. One preferred organic solvent for this purpose is isopropanol, although other suitable organic solvents can be used.

In an alternative methodology, wherein the solution does not include an organic solvent component, the homogenate is formed and an initial centrifugation step is performed to remove any unhomogenized tissue. Thereafter an effective amount of an organic solvent is added to preclude the solubilization of total RNA. This makes it possible to recover the RNA from the homogenate by a brief centrifugation (sedimentation). Preferably, the organic solvent added to precipitate RNA is added in a ratio of about 0.15–0.3 volumes of solvent per one volume of initial homogenate. Once separated, the RNA is washed with ethanol and the RNA precipitate may be dissolved in formamide and stored at −20° C. The use of formamide as a solubilization agent is beneficial in that it protects RNA from degradation by RNase, which may otherwise contaminate the isolated RNA.

Following precipitation of the RNA, DNA is precipitated by adding an additional 0.15–0.3 volumes of organic solvent per one volume of the initial homogenate. The DNA precipitate is removed from the homogenate by spooling or brief centrifugation (sedimentation). Proteins and other cellular components are retained in the homogenate and the protein component is precipitated by the addition of 3–4 volumes of an organic solvent per one volume of the initial homogenate.

Overall, and in comparison with other known methodologies, the precipitation of nucleic acids according to the present invention is performed with a substantially reduced amount of organic solvents. For example, in Sambrook, J. et al., "Molecular Cloning", Vol. 1, pp. 7.3–7.24, Cold Spring Harbor Press (1989), the precipitation of RNA requires the addition of 0.5–2.5 volumes of a lower alcohol added to one volume of the chaotropic solution. In addition, the RNA precipitation was carried out for several hours at −20–4° C. In contrast, the precipitation of RNA according to the present method is completed in about 3–5 minutes and is performed at room temperature. With respect to the DNA precipitation, Botwell, D. D. L. "Rapid Isolation of Eukaryotic DNA", Anal. Biochem. 162, 463–465 (1987), describes precipitation from chaotropic solutions carried out with 2–2.5 volumes of ethanol. Likewise, high volumes of alcohol have been recommended for the effective DNA precipitation from non-chaotropic solutions, as exemplified in Ausubel, F. M. et al., "Current Protocols in Molecular Biology", Vol. 1, pp. 221–245, John Wiley & Sons, Inc. (1994).

The unexpectedly low concentration of organic solvents required for precipitating RNA and DNA from the chaotropic solutions of the present invention makes it feasible to obtain RNA and DNA in highly pure form for use in molecular biology and biotechnology, as well as clinical research and other applications.

These and other features and advantages of the present invention will become apparent to persons skilled in the art upon review of the detailed description and working examples herein.

BRIEF DESCRIPTION OF THE DRAWINGS

FIG. 1B shows the utility of the total RNA in RT-PCR;

FIG. 1C shows the utility of the genomic DNA in PCR;

FIG. 1D shows the results of protein analysis by Western blotting;

FIG. 2B shows the results of total RNA analysis by Northern blotting;

FIG. 2C shows the results of genomic DNA analysis by Southern blotting;

FIG. 2D shows the results of protein analysis by Western blotting; and

DETAILED DESCRIPTION OF THE INVENTION

Figure 1A:
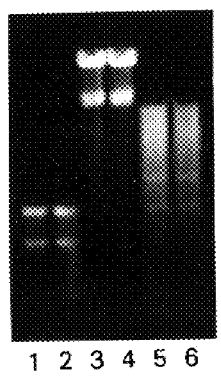
FIG. 1A shows the electrophoretic analysis of nucleic acids isolated in accordance with Example 1 herein.

Preferred solutions and methods according to the present invention are described in the following working Examples.

EXAMPLE 1

Simultaneous Isolation of DNA, RNA & Proteins From Cells

A method of the invention was used to simultaneously isolate DNA, RNA and proteins from rat somatomammotroph P0 cells. About $10^8$ P0 cells were lysed (homogenized) in a 10 ml of solution of the invention, which contained: 4M guanidine thiocyanate (Amresco, Inc., Solon, Ohio), 17% isopropanol, 0.1M sodium acetate, 0.1M 2-aminoethanethiol hydrochloride (Sigma, St. Louis, Mo.) and 0.2% sarkosyl in water. The solution was adjusted to pH 7.0 with hydrochloric acid, Unless stated otherwise, chemical reagents were obtained from Fisher Scientific (Pittsburgh, Pa.). Next, 0.6 ml aliquots of the lysate (homogenate) were frozen or used immediately for the isolation. The 0.6 ml aliquot utilized as described below contained 37.3 μg DNA, as determined by the diphenylamine reaction.

RNA isolation. The lysate (0.6 ml) was centrifuged for 8 minutes at 10,000 g at room temperature to sediment total RNA. The post-RNA lysate was transferred to a fresh tube and saved for the DNA and protein isolation described below. The RNA pellet was washed with 1 ml of 95% ethanol by vortexing and pipetting off the ethanol. Finally, RNA was dissolved in formamide and stored at −20 C. The total RNA isolation was completed in 11 minutes. The isolated RNA exhibited a 260/280 ratio of 1.79±0.05, with a yield of 49.2±2.8 μg RNA (mean±SD, n=3). Northern blotting of the isolated RNA preparations showed an undegraded pattern of mRNA when tested for growth hormone, prolactin, β-actin and GAPDH mRNAs.

For use in the reverse transcription PCR (RT-PCR), an aliquot of the RNA-solubilized formamide was precipitated with 3 volumes of ethanol. The precipitate was dissolved in water and used for RT-PCR.

It has been found that spectrophotometrical measurements to determine the optical density of RNA and DNA are substantially improved when performed in a solution containing higher than usual concentrations of chelating agents. For this purpose, the concentration of chelating agent(s) should be higher than 5 mM, with the optimum for ethylenediamine tetraacetate (EDTA) at 10 mM and for citrate at 30 mM. This is a new and unexpected finding. Typically, optical density readings of RNA and DNA are performed in water or 1 mM EDTA.

At higher concentration of chelating agents, the optical density readings are more reproducible and result in a higher 260/280 ratio. For example, the RNA preparation described in Example 1 had a 260/280 ratio of 1.79±0.05 when measured in water, and a ratio of 1.97±0.01 when measured in 10 mM EDTA.

DNA isolation. DNA was precipitated from the post-RNA lysate by the addition of 0.15 ml of isopropanol. The floating DNA precipitate was swirled (spooled) onto the pipette tip and transferred to a new tube. The remaining post-DNA lysate was saved for the protein isolation described below. The DNA was washed by mixing it with 1 ml of 95% ethanol and pipetting out the ethanol wash. The final DNA preparation was dissolved in 8 mM NaOH by gentle pipetting followed by neutralization of the solution with N-[2-hydroxyethyl] piperazine-N-[2-ethane sulfinic acid] (HEPES, free acid). The isolation was completed in less than 14 minutes. The isolated DNA exhibited a 260/280 ratio 1.81±0.02 (SD, n=3), indicating a lack protein contamination. The average yield from three isolations was 33.9±2.9 (SD, n=3) µg DNA. As compared with the original amount of DNA in the lysate, determined by the diphenylamine reaction, the method of the invention provided 91% recovery of DNA.

Protein isolation. Proteins were precipitated from the post-DNA lysate by the addition of 1.8 ml of isopropanol and centrifugation at 10,000 g for 5 minutes. The precipitate was washed with 95% ethanol and dissolved in 0.1N acetic acid. Alternatively, the precipitate could be dissolved in 0.1% sodium dodecylsulphate, or in water. The protein isolation was completed in 22 minutes. The isolated protein preparation was tested by Western blotting using a specific anti-rat prolactin antibody. The presence of the prolactin specific band in Western blotting is indicative of the good quality of the isolated protein preparation.

The results of tests performed with the simultaneously isolated RNA, DNA and proteins are shown in FIG. 1. FIG. 1 A shows the results of nucleic acids electrophoresed in 1% agarose gel and stained with ethidium bromide. Lanes 1 and 2 show undegraded total RNA (3 µg/lane); lanes 3 and 4 show high molecular weight genomic DNA (3 µg/lane); and lanes 5 and 6 show genomic DNA (3 µg) digested for 2 hours with EcoR1 restrictase. As the results demonstrate, there is no detectable DNA in the RNA preparation and no detectable RNA in the DNA preparation. The total digestion of DNA by EcoR1 restrictase is indicative of the good quality of the isolated DNA. FIGS. 1B–D show the results of RT-PCR, PCR and Western blotting performed with total RNA, genomic DNA and proteins, respectively, isolated as described hereinabove. The RT-PCR (FIG. 1B) and PCR (FIG. 1C) were performed using glyceraldehyde-3-phosphate dehydrogenase (GAPDH) and rat growth hormone (GH) primers, respectively, and Western blotting (FIG. 1C) was performed using anti-rat prolactin antibody. Amplification of the 374 base pair GAPDH DNA fragment in RT-PCR and the 686 base pair GH DNA fragment in PCR indicates that the isolated nucleic acid preparations (RNA and DNA) are adequately purified for the PCR reaction. Also, the presence of a prolactin specific band in Western blotting shows the high quality of the isolated protein preparation.

Similar results in the simultaneous isolation of RNA, DNA and proteins have been obtained when, in place of isopropanol, other water miscible organic solvents such as ethanol, methanol, acetone, dimethylsulfoxide, polyethylene glycol or mixtures of these solvents are used. These water miscible organic solvents can be used as components of the lysing solution and/or as the precipitating agents. All solvents are available from companies such Aldrich Chemical Co., Inc. (Milwaukee, Wis.) or Fluka Chemical Corp. (Ronkonkoma, N.Y.).

EXAMPLE 2

Simultaneous Isolation of RNA, DNA and Proteins From Tissues

In this embodiment of the method, the solution does not include an organic solvent component. This permits the removal of any unhomogenized tissue fragments from the lysate (homogenate) by a brief initial centrifugation. Thereafter, RNA is precipitated from the clear lysate by the addition of 0.2–0.3 volumes of an organic solvent.

Figure 2A:
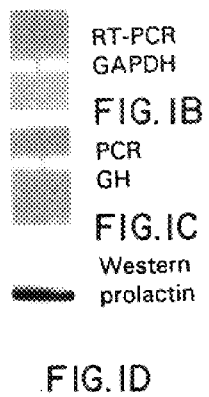
FIG. 2A shows the electrophoretic analysis of nucleic acids isolated in accordance with Example 2 herein.
Figure 2A:
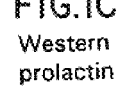
Figure 2A:
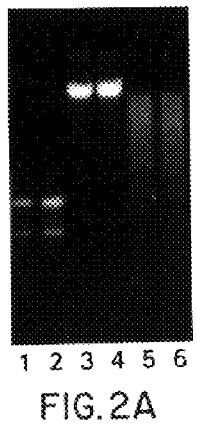

A frozen sample of rat pituitary was homogenized in a hand held glass-Teflon homogenizer with 1 ml of a lysing solution containing 4M guanidine thiocyanate, 0.1M sodium acetate, 0.1M 2-aminoethanethiol hydrochloride and 0.2% sarkosyl in water. The solution was adjusted to pH 7.0 with hydrochloric acid. The homogenate was centrifuged at 10,000 g for 5 minutes. The clear supernatant was transferred to a new tube, mixed with 0.3 ml of isopropanol and stored for 3 minutes at room temperature to precipitate RNA. The precipitated RNA was removed by centrifugation at 10,000 g for 8 minutes and dissolved in formamide. The post-RNA supernatant was further processed to isolate DNA and proteins in the same manner as described in Example 1. DNA and proteins were successively precipitated from the post-RNA lysate by the addition of 0.5 ml acetone and 10.75 ml of acetone, respectively. The isolated RNA exhibited a 260/280 ratio of 1.74 and the yield was 0.06 mg. The DNA exhibited a 260/280 ratio of 1.78 and the yield was 0.04 mg. As shown in FIG. 2A, there was no detectable DNA present in the RNA preparation and no detectable RNA present in the DNA preparation. As in FIG. 1A, the nucleic acids were electrophoresed in 1% agarose gel and stained with ethidium bromide. Lanes 1 and 2, total RNA (3 µg/lane); lanes 3 and 4, genomic DNA (3 µg/lane); and lanes 5 and 6, genomic DNA (3 µg) digested for 2 hours with EcoR1 restrictase.

The preparations of total RNA, genomic DNA and proteins were tested by Northern, Southern and Western blotting for the rat growth hormone (GH) mRNA, GH gene, and GH, respectively. All three analyses, depicted in FIGS. 2B–D, respectively, show that the method of invention yielded high quality RNA, DNA and protein preparations.

EXAMPLE 3

Isolation of RNA From Cells without Centrifugation of the Initial Lysate

Breast tumor MCF7 cells were grown in monolayer culture in a 3.5 cm petri dish. At the end of the culture period, the culture medium was removed and the cells were lysed by adding 1 ml of the lysing solution directly to the culture dish. The lysing solution used was that in Example 1. The lysate was centrifuged at 10,000 g for 5 minutes, and the RNA pellet was washed with 95% ethanol and dissolved in formamide. The isolated RNA exhibited a 260/280 ratio 1.81 and the yield was 22 µg RNA.

EXAMPLE 4

Isolation of RNA from Tissue with Centrifugation of the Initial Lysate to Remove Tissue Fragments Rat kidney (0.95 g) was homogenized in 19 ml of a lysing solution having the following composition: 4M guanidine thiocyanate, 0.1M sodium acetate and 0.2% sarkosyl in water. The solution was adjusted to pH 7.0 with hydrochloric acid. The homogenate was centrifuged at 10,000 g for 5 minutes to remove unsolubilized material. The resulting supernatant was transferred to a new tube and RNA was precipitated from the supernatant by the addition of 3.8 ml (0.3 volume) of isopropanol and centrifugated at 10,000 g for 8 minutes. The RNA pellet was dissolved in formamide and stored at −20 C. The RNA preparation exhibited a 260/280 ratio 1.77 and the yield was 3.9 mg of RNA.

EXAMPLE 5

Isolation of DNA from Cells without Centrifugation

The lysing solution used for this DNA isolation contained the following: 4M guanidine thiocyanate, 0.1M sodium acetate, 17% isopropanol, 0.2% sarkosyl in water. The lysing solution was adjusted to pH 9 by the addition of 0.4M NaOH.

Rat pituitary P0 cells were lysed in the lysing solution by repetitive pipetting. The lysate was mixed with 0.4 volume of ethanol and the precipitated DNA was spooled onto a pipette tip and washed twice with 95% ethanol. The resulting DNA was dissolved in 8 mM NaOH and neutralized to pH 8.0 with 0.1M HEPES buffer.

Figure 3:
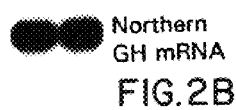
FIG. 3 shows the results of genomic DNA analysis by electrophoresis as isolated in Example 5.
Figure 3:
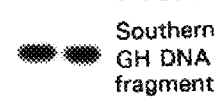
Figure 3:
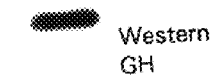
Figure 3:
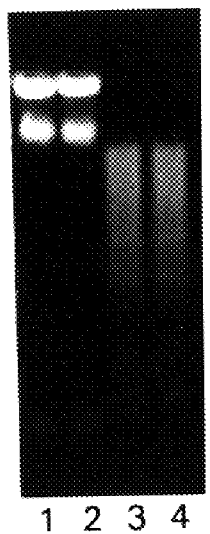

This embodiment of the invention further shortens the DNA isolation protocol by omitting centrifugation of the lysate. This deletion of centrifugation results in only a minor contamination of the isolated DNA with RNA. Analysis of the genomic DNA isolated as described above was performed by electrophoreses thereof in 1% agarose gel and staining with ethidium bromide. Lanes 1 and 2 of FIG. 3 are genomic DNA (3 µg/lane), and lanes 3 and 4 are genomic DNA digested for 2 hours with EcoR1. As is apparent in FIG. 3, only a residual amount of RNA was detected in the low molecular weight region of the agarose gel by the ethidium bromide staining. Apparently, spooling DNA onto a pipette tip removes mainly DNA, while most of the partially hydrolyzed RNA (as indicated by its low molecular weight) remains in the lysate. The presence of a reducing agent is not necessary for the isolation of DNA and the lysing solution can have pH within the range 6–12. The alkaline pH can be adjusted with NaOH, KOH or other organic or inorganic alkaline reagents. The best results are believed to be obtained when the lysate has a pH between 8–9.

The unexpected and rapid hydrolysis of RNA occurring at pH 8–pH 9 can be attributed to the presence of the chaotropic agent. This new finding allows for isolation of good quality DNA in a simple, one-step method.

The protocol for DNA isolation without centrifugation can be completed in less than 10 minutes. This is believed to be the fastest and simplest method of genomic DNA isolation. Importantly, the only equipment required for this method are tubes and pipettes. This allows for performing the DNA isolation on a field trip or elsewhere with a limited access to laboratory equipment.

EXAMPLE 6

Isolation of DNA from Tissues with One Centrifugation of the Lysate

Rat spleen (127 mg) was homogenized in a hand held glass-Teflon homogenizer with 5 ml of the lysing solution described in Example 5. The homogenate was centrifuged at 10,000 g for 5 minutes. The supernatant was transferred to a new tube and DNA was precipitated and washed as in Example 5. The isolated DNA exhibited a 260/280 ratio 1.76, and the yield was 1.93 mg DNA.

The scope of the present invention is not intended to be limited to the specific Examples described herein, but is to be accorded a scope commensurate with the appended claims.

What is claimed is:

1. A solution for isolating substantially pure and undegraded RNA, DNA and proteins from biological material, said solution comprising:
   at least one chaotropic agent,
   a buffer present in an amount sufficient to maintain the pH of said solution in the range of about 6 to about 7.5.
   an organic solvent present at a concentration in the range of about 13 to about 23% (v/v) of said solution, and
   at least one chelating agent.

2. The solution of claim 1 wherein said chelating agent is selected from the group consisting of ethylenediamine tetraacetic acid and citric acid.

3. The solution of claim 1 further comprising a detergent.

4. The solution of claim 3 wherein said detergent is selected from the group consisting of sarcosine and polyoxyethylenesorbitan.

5. A method of isolating substantially pure and undegraded RNA, DNA and proteins from biological material, comprising the steps of:
   a) homogenizing a biological material sample in the solution of claim 2 to form an homogenate;
   b) recovering substantially pure, undegraded RNA from the homogenate by sedimentation;
   c) thereafter precipitating DNA in the remaining homogenate by adding an additional amount of organic solvent thereto, and recovering the precipitated DNA by one of sedimentation or spooling; and
   d) thereafter precipitating proteins from the remaining homogenate by adding an additional amount of organic solvent thereto, and recovering the precipitated proteins by sedimentation.

6. The method of claim 5 wherein said additional amount of organic solvent added to precipitate DNA is added to achieve a concentration in the range of about 28 to about 38% (v/v).

7. The method of claim 6 wherein said organic solvent is selected from the group consisting of lower alcohols, acetone, polyethylene glycol and dimethylsulfoxide.

8. The method of claim 5 wherein said additional amount of organic solvent added to precipitate proteins is added to achieve a concentration in the range of about 78 to about 82% (v/v).

9. The method of claim 8 wherein said organic solvent is selected from the group consisting of lower alcohols, acetone, polyethylene glycol and dimethylsulfoxide.

10. A method of isolating substantially pure and undegraded RNA from biological material, comprising the steps of:
   a) homogenizing a biological material sample in a solution of claim 1 to form an homogenate; and
   b) recovering substantially pure RNA from the homogenate by sedimentation.

11. A method of isolating substantially pure and undegraded DNA from biological material, comprising the steps of:
   a) homogenizing a biological material sample in a solution of claim 1 to form an homogenate; and
   b) precipitating DNA in the homogenate by adding an additional amount of an organic solvent thereto for a concentration of organic solvent in the range of about 28% to about 38% (v/v), and recovering the precipitated DNA by one of spooling and sedimentation.

12. The method of claim 11 wherein said organic solvent is selected from the group consisting of lower alcohols, acetone, polyethylene glycol and dimethylsulfoxide.

13. A method of isolating substantially pure and undegraded RNA, DNA and proteins from biological material, comprising the steps of:
   a) homogenizing a biological material sample in a solution comprising:
      at least one chaotropic agent, and
      a buffer present in an amount sufficient to maintain the pH of said solution in the range of about 6 to about 7.5, to form an homogenate;
   b) removing unhomogenized material from the homogenate by sedimentation;
   c) precipitating RNA in the remaining homogenate by adding thereto an organic solvent to achieve a concentration in the range of about 13 to about 23% (v/v), and recovering the precipitated RNA by sedimentation;
   d) thereafter precipitating DNA in the remaining homogenate by adding an additional amount of organic solvent thereto, and recovering the precipitated DNA by one of spooling or sedimentation; and
   e) thereafter precipitating proteins from the remaining homogenate by adding an additional amount of an organic solvent thereto, and recovering the precipitated proteins by sedimentation.

14. The method of claim 13 wherein said organic solvent used for precipitating RNA is selected from the group consisting of lower alcohols, acetone, polyethylene glycol and dimethysulfoxide.

15. The method of claim 13 wherein said additional amount of organic solvent added to precipitate DNA is added to achieve a concentration in the range of about 28 to about 38% (v/v).

16. The method of claim 15 wherein said organic solvent is selected from the group consisting of lower alcohols, acetone, polyethylene glycol and dimethylsulfoxide.

17. The method of claim 13 wherein said additional amount of organic solvent added to precipitate proteins is added to achieve a concentration in the range of about 78 to about 82% (v/v).

18. The method of claim 17 wherein said organic solvent is selected from the group consisting of lower alcohols, acetone, polyethylene glycol and dimethylsulfoxide.

19. A method of isolating substantially pure and undegraded RNA from biological material, consisting essentially of the following steps:
   a) homogenizing a biological material sample in a solution consisting essentially of:
      at least one chaotropic agent, and
      a buffer present in an amount sufficient to maintain the pH of said solution in the range of about 6 to about 7.5, to form an homogenate;
   b) removing unhomogenized material from the homogenate by sedimentation; and
   c) precipitating RNA in the homogenate by adding thereto an organic solvent to achieve a concentration in the range of about 13 to about 23% (v/v), and recovering the precipitated RNA by sedimentation.

20. The method of claim 19 wherein said organic solvent is selected from the group consisting of lower alcohols, acetone, polyethylene glycol and dimethylsulfoxide.

21. A method of isolating substantially pure and undegraded DNA from biological material, consisting essentially of the following steps:
   a) homogenizing a biological material in a solution comprising:
      at least one chaotropic agent, and
      a buffer present in an amount sufficient to maintain the pH of said solution in the range of about 8 to about 12, to form an homogenate;
   b) removing unhomogenized material from the homogenate by sedimentation, and
   c) precipitating DNA in the homogenate by adding thereto an organic solvent to achieve a concentration in the range of about 28 to about 38% (v/v), and recovering the precipitated DNA by one of spooling or sedimentation.

22. The method of claim 21 wherein said organic solvent is selected from the group consisting of lower alcohols, acetone, polyethylene glycol and dimethylsulfoxide.

* * * * *

UNITED STATES PATENT AND TRADEMARK OFFICE
CERTIFICATE OF CORRECTION

PATENT NO.   : 5,945,515
DATED        : August 31, 1999
INVENTOR(S)  : Piotr Chomczynski It is certified that error appears in the above-indentified patent and that said Letters Patent is hereby corrected as shown below:

column 10, line 42, please replace "2" with --1--.

Signed and Sealed this

Thirteenth Day of February, 2001

*Attest:*

NICHOLAS P. GODICI

*Attesting Officer*   Acting Director of the United States Patent and Trademark Office